United States Patent
Bacque et al.

(12)

(10) Patent No.: US 6,872,740 B2
(45) Date of Patent: Mar. 29, 2005

(54) USE OF 2-AMINO-4-HETEROARYLETHYL-THIAZOLINE DERIVATIVES AS INHIBITORS OF INDUCIBLE NO-SYNTHASE

(75) Inventors: Eric Bacque, Gif sur Yvette (FR); Antony Bigot, Massy (FR); Jean-Christophe Carry, Saint Maur des Fosses (FR); Serge Mignani, Chatenay-Malabry (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/291,110

(22) Filed: Nov. 8, 2002

(65) Prior Publication Data

US 2003/0225140 A1 Dec. 4, 2003

Related U.S. Application Data

(60) Provisional application No. 60/352,977, filed on Jan. 30, 2002.

(30) Foreign Application Priority Data

Nov. 9, 2001 (FR) .............................................. 0114509

(51) Int. Cl.[7] ..................... A61K 31/431; C07D 409/06
(52) U.S. Cl. ....................................... 514/370; 548/199
(58) Field of Search ........................... 514/370; 548/199

(56) References Cited

FOREIGN PATENT DOCUMENTS

| WO | WO 94/12165 | 6/1994 |
|----|-------------|--------|
| WO | WO 95/11231 | 4/1995 |
| WO | WO 96/14842 | 5/1996 |

OTHER PUBLICATIONS

Creeke Paul et al, Synthesis and Elaboration of Heterocycles Via Iodocyclisation of Unsaturated Thioureas, Tetrahedron, (1989, pp. 4435–4438, vol. 30, No. 33).

Mark Sabat et al., Synthesis of Unnatural Amino Acids via Suzuki Cross–Coupling of Enantiopure Vinyloxazolidine Derivatives, Organic Letters (2000, pp. 1089–1092, vol. 8, No. 8).

Yoshiya Noike, Syntheses of quinolizine derivatives. VI. Syntheses of 3Oaminoquinolizines. 1. Syntheses of Heterocyclic Compounds (1960, pp. 11021 b).

*Primary Examiner*—Patricia L. Morris
(74) *Attorney, Agent, or Firm*—James W. Bolcsak; Irving Newman

(57) ABSTRACT

The present invention relates to the use of 2-amino-4-heteroarylethyl-thiazoline derivatives of formula (I)

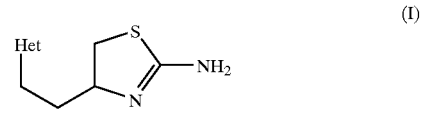

(I)

in which Het represents a thienyl, pyrimidyl, pyridyl or thiazolyl radical or pharmaceutically acceptable salts thereof as inhibitors of inducible NO-synthase.

6 Claims, No Drawings

USE OF 2-AMINO-4-HETEROARYLETHYL-THIAZOLINE DERIVATIVES AS INHIBITORS OF INDUCIBLE NO-SYNTHASE

This application claims the benefit of U.S. Provisional Application No. 60/352,977, filed Jan. 30, 2002, which claims the benefit of priority of French Patent Application No. 01/14,509, filed Nov. 09, 2001.

The present invention relates to the use of 2-amino-4-heteroarylethyl-thiazoline derivatives of formula (I):

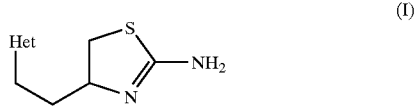

or pharmaceutically acceptable salts thereof as inhibitors of inducible NO-synthase.

The subject of the invention is the use of 2-amino-4-heteroarylethyl-thiazoline derivatives of formula (I) and pharmaceutically acceptable salts thereof for the preparation of pharmaceutical compositions intended for preventing and treating diseases in which an abnormal production of nitric oxide (NO) by induction of inducible NO-synthase (NOS-2 or iNOS) is involved, the pharmaceutical compositions containing the novel 2-amino-4-heteroarylethyl-thiazoline derivatives and pharmaceutically acceptable salts thereof and the novel derivatives of 2-amino-4-heteroarylethyl-thiazoline and pharmaceutically acceptable salts thereof.

Nitric oxide (NO) is a diffusable radical involved in many physiological and pathological processes. It is synthesized by the oxidation of L-Arginine, a reaction catalyzed by a family of enzymes known as nitric oxide synthases or NO-Synthase (NOS), referenced in the international enzyme nomenclature under the number E.C. 1.14.13.39.

Three NOS isoforms, two of which are constitutive and one inducible, are known:
- a neuronal NOS (NOS-1 or nNOS) was originally isolated and cloned from nerve tissue in which it is a constitutive enzyme. The NOS-1 produces NO in response to various physiological stimuli such as the activation of membrane receptors according to a mechanism dependent on calcium and on calmodulin.
- an inducible NOS (NOS-2 or iNOS) can be induced in response to immunological stimuli such as, for example, cytokines or bacterial antigens in various cells such as, for example, macrophages, endothelial cells, hepatocytes, glial cells, as well as many other types of cells. This isoform activity is not regulated by calcium. Consequently, once induced, it produces a large amount of NO over prolonged periods.
- an endothelial NOS (NOS-3 or eNOS) is constitutive and calcium/calmodulin dependent. It was originally identified in vascular endothelium cells, in which it generates NO in response to physiological stimuli such as the activation of membrane receptors.

The NO produced by the neuronal and endothelial constitutive isoforms (NOS-1 and NOS-3) is generally involved in intercellular signalling functions. For example, the endothelial cells which line the inner wall of blood vessels induce the relaxation of the underlying smooth muscular cells via the production of NO. It thus contributes towards regulating the arterial pressure.

The NO produced in large amount by the inducible isoform NOS-2 is, inter alia, involved in the pathological phenomena associated with acute and chronic inflammatory processes in a large variety of tissues and organs.

An excessive production of NO by induction of NOS-2 thus plays a part in degenerative pathologies of the nervous system such as, for example, multiple sclerosis, focal or global cerebral ischemia, cerebral or spinal trauma, Parkinson's disease, Huntington's disease, Alzheimer's disease, amyotrophic lateral sclerosis, migraine, depression, schizophrenia, anxiety, epilepsy. Similarly, aside the central nervous system, the induction of NOS-2 is involved in many pathologies with inflammatory components such as, for example, diabetes, atherosclerosis, myocarditis, arthritis, arthrosis, asthma, inflammatory bowel disease, Crohn's disease, peritonitis, gastroesophageal reflux, uveitis, Guillain-Barré syndrome, glomerulo-nephritis, lupus erythematosus and psoriasis. The NOS-2 was also involved in the growth of certain forms of tumors such as, for example, epitheliomas, adenocarcinomas or sarcomas, and in infections with Gram-positive or Gram-negative intracellular or extracellular bacteria.

In all the situations in which an overproduction of NO is deleterious, it thus appears to be desirable to reduce the production of NO by administering substances capable of inhibiting the NOS-2. However, given the important physiological roles played by the constitutive isoform NOS-3, in particular in regulating the arterial pressure, it is essential that the inhibition of the isoform NOS-2 has the least possible effect on the isoform NOS-3. Actually, it is known that the administration of unselective inhibitors of NOS isoforms leads to vasoconstriction and an increase in arterial pressure (Moncada, S., Palmer, R. M. J. and Higgs, E. A., Biosynthesis of nitric oxide from L-arginine: a pathway for the regulation of cell function and communication, *Biochem. Pharmacol.*, 1989, 38: 1709–1715). These effects on the cardiovascular system are deleterious since they reduce the supply of nutrients to the tissues. Consequently, the present invention relates to compounds whose inhibitory activity with respect to NOS-2 is significantly higher than their inhibitory activity with respect to NOS-3.

Thiazoline-based NOS inhibitors are described in particular in patent applications WO94/12165, WO95/11231 and WO96/14842.

The present invention relates to the use of 2-amino-4-heteroarylethyl-thiazoline derivatives of formula (I) in which:

Het represents a 2-thienyl, 3-thienyl, 2-pyrimidyl, 5-pyrimidyl, 2-pyridyl, 3-pyridyl, 4-pyridyl, 2-thiazolyl, 4-thiazolyl or 5-thiazolyl radical for the preparation of useful medicinal products for preventing or treating diseases in which an abnormal production of nitric oxide (NO) by induction of inducible NO-synthase (NOS-2 or iNOS) is involved.

The compounds of formula (I) contain one or more asymmetric carbons and can thus be in racemic form or in the form of enantiomers and diastereoisomers; these also form a part of the invention as well as the mixtures thereof.

Moreover, the compounds of formula (I) may be in the tautomeric form (Ia):

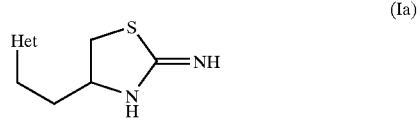

These tautomers also form a part of the invention.

Among the compounds of formula (I) useful according to the invention, mention may be made of the following compounds:

4-(2-pyridin-2-ylethyl)-4,5-dihydro-1,3-thiazol-2-ylamine,
4-(2-pyridin-3-ylethyl)-4,5-dihydro-1,3-thiazol-2-ylamine, The derivatives of formula (II) can be obtained according to the following reaction schemes:

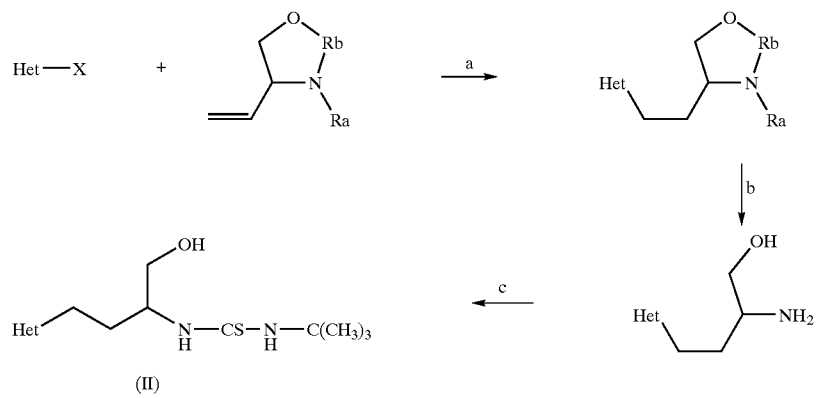

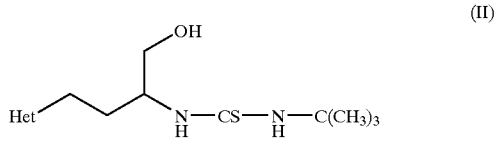

(II)

4-(2-pyridin-4-ylethyl)-4,5-dihydro-1,3-thiazol-2-ylamine, and
4-(2-thien-3-ylethyl)-4,5-dihydro-1,3-thiazol-2-ylamine,
the racemic mixtures, enantiomers, diastereoisomers, tautomers thereof, as well as the pharmaceutically acceptable salts thereof, and more particularly the following compounds:
(+)-(4R)-4-(2-pyridin-2-ylethyl)-4,5-dihydro-1,3-thiazol-2-ylamine,
(+)-(4R)-4-(2-pyridin-3-ylethyl)-4,5-dihydro-1,3-thiazol-2-ylamine,
(+)-(4R)-4-(2-pyridin-4-ylethyl)-4,5-dihydro-1,3-thiazol-2-ylamine, and
(4R)-4-(2-thien-3-ylethyl)-4,5-dihydro-1,3-thiazol-2-ylamine,
the tautomers thereof, as well as the pharmaceutically acceptable salts thereof.

Among the compounds of formula (I) useful according to the invention and particularly preferred, mention may be made of the following compound:
4-(2-thien-3-ylethyl)-4,5-dihydro-1,3-thiazol-2-ylamine,
the racemates, enantiomers, tautomers thereof, as well as the pharmaceutically acceptable salts thereof, The invention also relates to the pharmaceutical compositions containing, as active principle, a derivative of formula (I) for which Het represents a 2-thienyl, 3-thienyl, 2-pyrimidyl, 5-pyrimidyl, 2-pyridyl, 3-pyridyl, 4-pyridyl, 2-thiazolyl, 4-thiazolyl or 5-thiazolyl radical as well as the racemic mixtures, enantiomers, diastereoisomers thereof and mixtures thereof, the tautomers thereof and pharmaceutically acceptable salts thereof.

The compounds of formula (I) can be prepared by cyclization of a derivative of formula (II):

(II)

in which Het has the same meaning as in formula (I).

This cyclization is generally carried out using an acid such as hydrochloric acid, in aqueous medium, at a temperature of about 100° C. 6N hydrochloric acid is generally used.

In these formulae, Het has the same meanings as in formula (I), Ra is a protecting group of the amine function such as those described by T. W. GREENE, *Protective groups in Organic Synthesis*, J. Wiley-Interscience Publication (1991) and Rb is a protecting group of the β-amino alcohol function such as those described by T. W. GREENE, *Protective Groups in Organic Synthesis*, J. Wiley-Interscience Publication (1991). Preferably the protecting group of the amine function is an acetyl or tert-butyloxycarbonyl radical, and the protecting group of the β-amino alcohol function is an isopropylidene or a benzylidene radical. X represents a halogen atom, preferably bromine or iodine, or a perfluoroalkylsulfonate radical.

The reaction a is generally carried out in the presence of a derivative of boron such as 9-borabicyclononane or diisoamylborane in an aromatic solvent such as toluene or an etehereal solvent such as THF, at a temperature of between 10° C. and the boiling point of the reaction medium. Then, at the reaction medium is added an aqueous solution of metal alkaline hydroxide such as sodium or potassium hydroxide, followed with transition metal complex such as palladium tetrakistriphenylphosphine or palladium dichloride diphenylphosphinoferrocenyl, followed by Het-X. The resulting mixture is heated at a temperature of the boiling point of the reaction medium.

The deprotection reaction b for the compounds in which Ra is a protecting group of the amine function and Rb is a protecting group of the β-amino alcohol function is carried out by any method of deprotection known by those skilled in the art and particularly those described by T. W. GREENE, *Protective Groups in Organic Synthesis*, J. Wiley-Interscience Publication (1991). Preferably when the protecting group of the amine function is a tert-butyloxycarbonyl radical and the protecting group of the β-amino alcohol function is an isopropylidene or benzylidene radical, this reaction is carried out using an acid such as hydrochloric acid, in an aqueous medium, at a temperature of about 25° C. 6N hydrochloric acid is generally used. Similarly, when the protecting group of the amine function is an acetyl radical, and the protecting group of the β-amino alcohol function is an isopropylidene or benzylidene radical, this reaction is carried out using an acid such as hydrochloric acid, in an aqueous medium, at a temperature of about the boiling point of the reaction medium. 6N hydrochloric acid is generally used.

The reaction c is carried out by the action of tert-butyl isothiocyanate, in an inert solvent such as a ($C_1$–$C_4$) aliphatic alcohol (preferably methanol or ethanol), in the presence of a tertiary amine such as triethylamine, at a temperature of between 20° C. and the boiling point of the reaction medium.

The compounds of formula (I) are isolated and may be purified by the usual known methods, for example crystallization, chromatography or extraction.

The enantiomers of the compounds of formula (I) can be obtained by resolving the racemic mixtures, for example by chromatography on a chiral column according to PIRCKLE W. H. et al., *Asymmetric Synthesis*, Vol. 1, Academic Press (1983) or by formation of salts or by synthesis from chiral precursors. The diastereoisomers can be prepared according to the known conventional methods (crystallization, chromatography or from chiral precursors).

The compounds of formula (I) can optionally be converted to addition salts with an inorganic or organic acid by the the action of such an acid in an organic solvent such as an alcohol, a ketone, an ether or a chlorinated solvent. These salts also form a part of the invention.

Examples of pharmaceutically acceptable salts which may be mentioned are the following salts: benzenesulfonate, hydrobromide, hydrochloride, citrate, ethanesulfonate, fumarate, gluconate, iodate, isethionate, maleate, methanesulfonate, methylenebis-β-oxynaphtoate, nitrate, oxalate, pamoate, phosphate, salicylate, succinate, sulfate, tartrate, theophyllinacetate and p-toluenesulfonate.

The compounds of formula (I) are inhibitors of inducible NO-synthase or NO-synthase of type 2 (NOS-2) and are thus useful for preventing and treating disorders associated with an excessive NO production such as multiple sclerosis, focal or global cerebral ischemia, cerebral or spinal trauma, Parkinson's disease, Huntington's disease, Alzheimer's disease, amyotrophic lateral scherosis, migraine, depression, schizophrenia, anxiety, epilepsy, diabetes, atherosclerosis, myocarditis, arthritis, arthrosis, asthma, inflammatory bowel disease, Crohn's disease, peritonitis, gastro-esophageal reflux, uveitis, Guillain-Barré syndrome, glomerulonephritis, lupus erythematosus and psoriasis, the growth of certain forms of tumors such as for example epitheliomas, adenocarcinomas or sarcomas, and in infections with Gram-positive or Gram-negative intracellular or extracellular bacteria.

Their activities as inhibitors of NOS-2 and NOS-3 were determined by measuring the conversion of [$^3$H]-L-arginine into [$^3$H]-L-citrulline with, respectively, a NOS-2 enzymatic fraction extracted from the lungs of rats or mice pretreated with lipopolysaccharides (10 mg/kg i.p. 6 hours before collecting the tissue) and with a commercial preparation of recombinant bovine NOS-3. The compounds were incubated for 20 to 30 minutes at 37° C. in the presence of 5 µM (for NOS-2 activity) or 10 µM (for NOS-3 activity) of [$^3$H]-L-arginine, 1 mM of NADPH, 15 µM of tetrabiopterine, 1 µM of FAD, 0.1 mM of DTT in a HEPES buffer (50 mM, pH 6,7) containing 10 µg/ml of calmodulin and 1.25 mM of CaCl$_2$ when the NOS-3 activity was measured. The incubation was stopped by adding cold HEPES buffer (100 mM, pH 5.5) containing 10 mM EGTA and 500 mg of cationic ion-exchange resin (AG50W-X8, counter-ion: Na$^+$) to separate the [$^3$H]-L-arginine from the [$^3$H]-L-citrulline. After separation of the phases by settling for 5 min, the radioactivity remaining in the liquid phase was measured in a scintillation counter in the presence of a suitable scintillation liquid. The yield for the recovery of the formed L-[$^3$H]citrulline was able to be estimated using L-[ureido-$^{14}$C]-citrulline as external standard The NOS-2 or NOS-3 activity was expressed in picomole(s) of [$^3$H]-L-citrulline formed per minute and per milligram of protein contained in the rection medium.

In this test on the enzyme NOS-2, the IC$_{50}$ value for the compounds of formula (I) is less than or equal to 10 µM.

The selectivity is measured by the IC$_{50}$ NOS-3/IC$_{50}$ NOS-2 ratio. This selectivity is greater than 45.

The compounds of formula (I) are of low toxicity. Their LD$_{50}$ is greater than 40 mg/kg via cutaneous route in mice.

The following example illustrates the invention in a non exhaustive manner.

EXAMPLE 1

(4R)-4-(2-Thien-3-yl-ethyl)-4,5-dihydro-1,3-thiazol-2-ylamine, hydrochloride

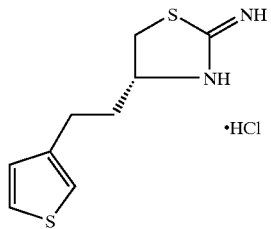

A mixture of 0.72 g of N-(tert-butyl)-N'-[(1R)-2-hydroxy-1-(2-thien-3-yl-ethyl)ethyl]-thiourea in 20 mL of aqueous solution of 5N hydrochloric acid is heated under magnetic stirring at a temperature of about 100° C. for 18 hours. The reaction medium is then evaporated under reduced pressure (2 kPa) at a temperature of about 40° C. and the residue obtained is taken up in 20 mL of ethanol and concentrated again according to the conditions described above. The evaporating residue is taken up in 5 mL of ethanol, filtered, washed with 2 times 2 mL of ethanol and with 2 times 5 mL of ethyl ether. The product is dried in an oven under vacuum (10 Pa) at a temperature of about 20° C. About 0.28 g of (4R)-4-(2-thien-3-ylethyl)-4,5-dihydro-1,3-thiazol-2-ylamine, chlorhydrateare are obtained in the form of a colored-beige solid melting at 150° C. [$^1$H NMR spectrum (300 MHz, (CD$_3$)$_2$SO d6, δ in ppm): from 1.85 to 2.10 (mt, 2H); 2.70 (mt, 2H); from 3.30 to 3.45 (mt, 1H); 3.69 (dd, J=11 and 7.5 Hz, 1H); 4.21 (mt, 1H); 7.05 (dd, J=5 and 1.5 Hz, 1H); 7.26 (mt, 1H); 7.50 (dd, J=5 and 3 Hz, 1H); 9.10 (mf, 1H); 9.61 (mf, 1H); 10.27 (s large, 1H)].

N-(tert-Butyl)-N'-[(1R)-2-hydroxy-1-(2-thien-3-ylethyl)ethyl]-thiourea

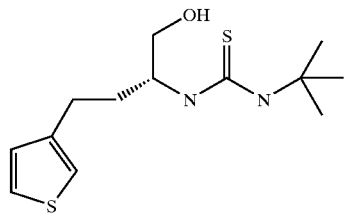

A solution of 1.2 g of (2R)-2-amino-4-(3-thienyl)-1-butanol, hydrochloride in 40 mL of ethanol, is combined with 1.1 mL of tert-butylisothiocyanate and 1 mL of triethylamine and magnetically stirred under inert atmosphere at a temperature of about 20° C., then heated for 20 hours at a temperature of about 50° C. The reaction medium is concentrated under reduced pressure (2 kPa) at a temperature of about 50° C. The solution is evaporated to obtain a residue, which is purified by chromatography under argon pressure (70 kPa), on a column of silica gel (particle size 60–200 μm; diameter 3.6 cm; height 20 cm), eluting with a mixture of cyclohexane-ethylacetate (60/40 by volume) and obtaining fractions of 30 mL. The fractions containing the expected product are collected and evaporated under reduced pressure (2 kPa) at a temperature of about 40° C. About 0.73 g of N-(tert-butyl)-N'-[(1R)-2-hydroxy-1-(2-thien-3-ylethyl) ethyl]thiourea are obtained in the form of a colorless oil. [$^1$H NMR spectrum (300 MHz, (CD$_3$)$_2$SO d6, δ in ppm): 1.42 (s, 9H); from 1.60 to 1.95 (mt, 2H); 2.60 (t large, J=8 Hz, 2H); 3.38 (mt, 1H); 3.50 (mt, 1H); 4.26 (mf, 1H); 4.80 (mf, 1H); 7.01 (dd, J=5 and 1.5 Hz, 1H); from 7.15 to 7.25 (mt, 2H); 7.20 (s, 1H); 7.46 (dd, J=5 and 3 Hz, 1H)].

(2R)-2-Amino-4-(3-thienyl)-1-butanol, hydrochloride

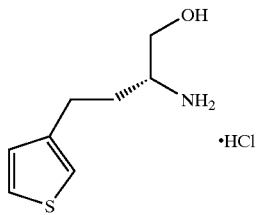

A suspension of 1.8 g of tert-butyl 2.2-dimethyl-4-(2-thien-3-yl-ethyl)-oxazolidine-3-carboxylate in 5 mL of an aqueous solution of 5N hydrochloric acid and 5 mL of dioxane is stirred at a temperature of about 20° C. for 3 hours. The reaction mixture is then concentrated under reduced pressure (2 kPa) at a temperature of about 40° C. About 1.3 g of (2R)-2-amino-4-(3-thienyl)-1-butanol, chlorhydrate are obtained in the form of a thick oil. [$^1$H NMR spectrum (300 MHz, (CD$_3$)$_2$SO d6, δ in ppm): from 1.70 to 1.95 (mt, 2H); 2.70 (t large, J=8 Hz, 2H); 3.05 (mt, 1H); 3.50 (dd, J=11 and 6 Hz, 1H); 3.64 (dd, J=11 and 4 Hz, 1H); 7.02 (dd, J=5 and 1.5 Hz, 1H); 7.23 (d large, J=3 Hz, 1H); 7.49 (dd, J=5 and 3 Hz, 1H); 8.02 (mf, 3H)].

(4R)-2,2-Dimethyl-4-(2-thien-3-yl-ethyl)-oxazolidine-3-tert-butyl carboxylate

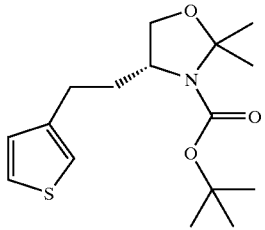

To a suspension of 1.5 g of (4R)-2,2-dimethyl-4-vinyl-oxazolidine-3-tert-butyl carboxylate in 33 mL of toluene, stirred under inert atmosphere, about 26.4 mL of a solution of 9-borabicyclo-[3.3.1]-nonane are added. The reaction medium is heated at a temperature of about 70° C. for 30 minutes. The heating is momentarily stopped to add 5.3 mL of an aqueous 5N sodium bicarbonate solution in 2 mL of water and after 1 minute, 0.23 g of tetrakis (triphenylphosphine)palladium(0) and 0.81 mL of 3-bromo-thiophene are added. The heating is continued for 22 hours at a temperature of about 90° C. After cooling the reaction mixture at a temperature of about 20° C., 100 mL of ethyl acetate are added. The organic phase is separated, dried over magnesium sulfate, filtered and concentrated under reduced pressure (2 kPa) at a temperature of about 40° C. The solvent is evaporated and the residue is purified by chromatography (70 kPa), on a column of silica gel (particle size 60–200 μm; diameter 3.6 cm; height 30 cm), eluting with mixture of cyclohexane-ethyl acetate (90/10 by volume) and obtaining fractions of 60 mL. The fractions containing the expected product are combined and concentrated under reduced pressure (2 kPa) at a temperature of about 40° C. About 1.8 g of (4R)-2,2-dimethyl-4-(2-thien-3-yl-ethyl)-oxazolidine-3-tert-butyl carboxylate are obtained in the form of a yellow oil. [$^1$H NMR spectrum (400 MHz, (CD$_3$)$_2$SO d6, at a temperature of 373 K, δ in ppm): 1.45 (s, 9H); 1.54 (s, 6H); from 1.75 to 2.10 (mt, 2H); 2.65 (mt, 2H); 3.75 (dd, J=9 and 2 Hz, 1H); 3.85 (mt, 1H); 3.94 (dd, J=9 and 6 Hz, 1H); 6.99 (d large, J=5 Hz, 1H); 7.14 (mt, 1H); 7.40 (dd, J=5 and 3 Hz, 1H)].

The pharmaceutical compositions according to the invention consist of a compound of formula (I) or an isomer or tautomer or salt of such a compound, in pure form or in the form of a composition in which it is combined with any other pharmaceutically compatible product, which may be inert or physiologically active. The medicinal products according to the invention may be used orally, parenterally, rectally or topically.

Solid compositions for oral administration which can be used include tablets, pills, powders (gelatin capsules, cachets) or granules. In these compositions, the active principle according to the invention is mixed with one or more inert diluents, such as starch, cellulose, sucrose, lactose ou silica, under a stream of argon. These compositions can also comprise substances other than diluents, for example, one or more lubricants such as magnesium stearate or talc, a dye, a coating (dragées) or a varnish.

Liquid compositions for oral administration which can be used include pharmaceutically acceptables solutions, suspensions, emulsions, syrups and elixirs containing inert diluents such as water, ethanol, glycerol, plant oils or liquid paraffin. These compositions can comprise substances other than diluents, for example, wetting products, sweeteners, thickeners, flavorings or stabilizers.

The sterile compositions for parenteral administration can preferably be aqueous or non-aqueous solutions, suspensions or emulsions. Solvent or vehicles which may be used include water, propylene glycol, a polyethylene glycol, plant oils, in particular olive oil, injectable organic esters, for example ethyl oleate, or other suitable organic solvents. These compositions can also contain adjuvants, in particular, wetting agents, isotonic agents, emulsifiers, dispersants and stabilizers. The sterilization can be carried out in several ways, for example by aseptic filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semi-synthetic glycerides or polyethylene glycols.

The compositions for topical administration can be, for example, creams, lotions, eye drops, mouth washes, nasal drops or aerosols.

In human therapy, the compounds according to the invention are particularly useful for treating and/or preventing multiple sclerosis, focal or global cerebral ischemia, cerebral or spinal trauma, Parkinson's disease, Huntington's disease, Alzheimer's disease, amyotrophic lateral scherosis, migraine, depression, schizophrenia, anxiety, epilepsy, diabetes, atherosclerosis, myocarditis, arthritis, arthrosis, asthma, inflammatory bowel disease, Crohn's disease, peritonitis, gastro-esophageal reflux, uveitis, Guillain-Barré syndrome, glomerulo-nephritis, lupus erythematosus, psoriasis, the growth of certain forms of tumors such as, for example, epitheliomas, adenocarcinomas or sarcomas, and in infections with Gram-positive or Gram-negative intracellular or extracellular bacteria.

The doses depend on the desired effect, the duration of the treatment and the route of administration used; they are generally comprised between 1 mg and 100 mg per day via the oral route for an adult, with unit doses ranging from 0.5 mg to 50 mg of active substance.

The examples which follow illustrate compositions according to the invention:

EXAMPLE A

Gel capsules containing 50 mg of active product and having the composition below are prepared, according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50 mg of active product and having the composition below are prepared, according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol, titanium oxide (72/3.5/24.5) q.s. 1 finished film-coated tablet weighing | 245 mg |

EXAMPLE C

An injectable solution containing 10 mg of active product having the following composition:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water q.s | 4 ml |

The present invention also relates to the method for preventing and treating diseases in which an abnormal production of nitric oxide (NO) by induction of inducible NO-synthase (NOS-2 or iNOS) is involved by administration of a compound of formula (I), the racemic mixtures, enantiomers, diastereoisomers thereof and mixtures thereof, tautomer thereof and pharmaceutically acceptable salts thereof.

We claim:

1. A compound of the formula (I)

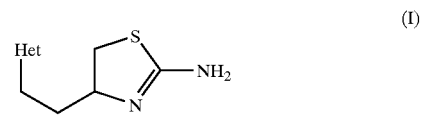

(I)

wherein Het is 2-thienyl, 3-thienyl, or
a racemic mixture, an enantiomer, a diastereoisomer or a mixture thereof, a tautomer thereof, or a pharmaceutically acceptable salt thereof.

2. The compound according to claim 1, wherein the compound of formula (I) is
4-(2-thien-3-ylethyl)-4,5-dihydro-1,3-thiazol-2-ylamine, or
a racemic mixture, an enantiomer, a diastereoisomer or a mixture thereof, a tautomer thereof, or a pharmaceutically acceptable salt thereof.

3. The compound according to claim 1, wherein the compound of formula (I) is
(4R)-4-(2-thien-3-ylethyl)-4,5-dihydro-1,3-thiazol-2-ylamine, or
a tautomer thereof or a pharmaceutically acceptable salt thereof.

4. A pharmaceutical composition comprising, as active ingredient, one or more compound of formula (I):

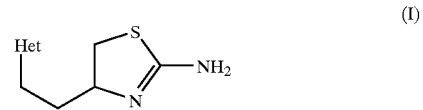

(I)

wherein Het is 2-thienyl, 3-thienyl, or
a racemic mixture, an enantiomer, a diastereoisomer or a mixture thereof, a tautomer thereof, or a pharmaceutically acceptable salt thereof, in combination with a pharmaceutically acceptable carrier.

5. The composition according to claim 4, wherein the compound of formula (I) is
4-(2-thien-3-ylethyl)-4,5-dihydro-1,3-thiazol-2-ylamine, or
a racemic mixture, an enantiomer, a diastereoisomer or a mixture thereof, a tautomer thereof, or a pharmaceutically acceptable salt thereof.

6. The composition according to claim 4, wherein the compound of formula (I) is
(4R)-4-(2-thien-3-ylethyl)-4,5-dihydro-1,3-thiazol-2-ylamine, or
a tautomer thereof or a pharmaceutically acceptable salt thereof.

* * * * *